United States Patent
Guthermann

(10) Patent No.: US 6,411,832 B1
(45) Date of Patent: Jun. 25, 2002

(54) METHOD OF IMPROVING REPRODUCIBILITY OF NON-INVASIVE MEASUREMENTS

(75) Inventor: Howard E. Guthermann, Newton, MA (US)

(73) Assignee: Optix LP, Jupiter Island, FL (US)

( * ) Notice: Subject to any disclaimer, the term of this patent is extended or adjusted under 35 U.S.C. 154(b) by 0 days.

(21) Appl. No.: 09/465,105

(22) Filed: Dec. 16, 1999

Related U.S. Application Data

(63) Continuation-in-part of application No. 09/073,575, filed on May 6, 1998, now Pat. No. 6,222,189, which is a continuation-in-part of application No. 08/937,934, filed on Sep. 25, 1997, now Pat. No. 6,064,065, which is a division of application No. 08/479,955, filed on Jun. 7, 1995, now Pat. No. 5,672,875, which is a continuation-in-part of application No. 08/333,758, filed on Nov. 3, 1994, now Pat. No. 5,818,048, which is a continuation-in-part of application No. 08/182,572, filed on Jan. 14, 1994, now Pat. No. 5,424,545, which is a continuation-in-part of application No. 08/130,257, filed on Oct. 1, 1993, now Pat. No. 4,434,412, which is a continuation-in-part of application No. 07/914,265, filed on Jul. 15, 1992, now Pat. No. 5,321,265.

(51) Int. Cl.$^7$ ................................................. A61B 5/00
(52) U.S. Cl. ........................ 600/322; 600/328; 600/316
(58) Field of Search ................................. 600/309–310, 600/316, 322–324, 326, 328, 334–335, 340, 344; 356/39–41, 405; 250/343, 339

(56) References Cited

U.S. PATENT DOCUMENTS

| | | | |
|---|---|---|---|
| 4,805,623 A | 2/1989 | Jöbsis | |
| 5,313,941 A | 5/1994 | Braig et al. | |
| 5,321,265 A | 6/1994 | Block | 250/343 |
| 5,372,134 A * | 12/1994 | Richardson | 600/323 |
| 5,424,545 A | 6/1995 | Block et al. | 250/343 |
| 5,433,197 A | 7/1995 | Stark | |
| 5,434,412 A | 7/1995 | Sodickson et al. | 250/343 |
| 5,448,992 A | 9/1995 | Kupershmidt | |
| 5,542,421 A * | 8/1996 | Erdman | 600/477 |
| 5,672,875 A | 9/1997 | Block et al. | 250/343 |
| 5,818,044 A | 10/1998 | Sodickson et al. | 250/339.06 |
| 5,818,048 A | 10/1998 | Sodickson et al. | 250/343 |
| 5,956,144 A | 9/1999 | Kaplan | |
| 6,026,313 A * | 12/2000 | Kexin | 600/310 |
| 6,222,189 B1 * | 4/2001 | Misner et al. | 250/341.1 |
| 6,224,548 B1 * | 5/2001 | Gopinathan et al. | 600/300 |

FOREIGN PATENT DOCUMENTS

| | | |
|---|---|---|
| WO | WO 93/07801 A1 | 4/1993 |
| WO | WO 00/62661 A1 | 10/2000 |

OTHER PUBLICATIONS

Kim et al. "Pulse Oximetry and Circulatory Kinetics Associated with Pulse Volume Amplitude Measured by Photoelectric Plethysmography," Anesth. Analg. 65:1333–39 (1986).

\* cited by examiner

Primary Examiner—Eric F. Winakur
Assistant Examiner—Matthew J Kremer
(74) Attorney, Agent, or Firm—Lahive & Cockfield, LLP

(57) ABSTRACT

A method of improving the accuracy and reproducibility of non-invasive measurements of a concentration of a constituent of interest carried in a body part has been developed. The method relies on elevating the body part during the measurement cycle so that the body part is maintained above the heart during the measurement cycle. Measurements of the constituent during an arterial pulse leads to improved intra-run and run-to-tun determinations.

13 Claims, 3 Drawing Sheets

METHOD OF IMPROVING REPRODUCIBILITY OF NON-INVASIVE MEASUREMENTS

REFERENCE TO RELATED APPLICATIONS

This application is a continuation-in-part of U.S. patent application Ser. No. 09/073,575, filed on May 6, 1998 now U.S. Pat. No. 6,222,189, entitled "Methods of Enhancing Optical Signals by Mechanical Manipulation in Non-Invasive Testing," which is a continuation-in-part of U S. patent application Ser. No. 08/937,934, filed on Sep. 25, 1997, now U.S. Pat. No. 6,064,065, which is a divisional of U.S. patent application Ser. No. 08/479,955, filed on Jun. 7, 1995, now U.S. pat. No. 5,672,875, which is a continuation-in-part of U.S. patent application Ser. No. 08/333,758, filed on Nov. 3, 1994, now U.S. Pat. No. 5,818,048, which is a continuation-in-part of U.S. patent application Ser. No. 08/182,572, filed on Jan. 14, 1994, now U.S. Pat. No. 5,424,545, which is a continuation-in-part of U.S. patent application Ser. No. 08/130,257, filed on Oct. 1, 1993, now U.S. Pat. No. 4,434,412, which is a continuation-in-part of U.S. patent application No. 07/914,265, filed on Jul. 15, 1992, now U.S. Pat. No. 5,321,265.

GOVERNMENT SUPPORT

Work described herein was funded, in part, by one or more grants awarded by the Department of Health and Human Services. The U.S. Government, therefore, may have certain rights in this invention.

BACKGROUND OF INVENTION

The present invention relates to a method of improving the reproducibility of non-invasive measurements of concentration of constituents in arterial blood, primarily spectroscopic and Kromoscopic measurements. In particular, the invention uses a mechanical method, elevation of the measurement site above the heart, to provide greater reproducibility of results.

One of the major problems with spectroscopic and other non-invasive measurements is the reproducibility of results. While measurements may be made which give results that can be correlated with invasive measurements, there are often problems reproducing the run-to-run results and even inconsistency among the data within a run. Although the use of methods such as Kromoscopy, the basics of which are described in the U.S. Pat. No. 5,321,265 entitled NON-INVASIVE TESTING, can provide sufficiently sensitive measurements in order to provide blood glucose or hemoglobin concentration, even these improved measurements may be plagued by the problems of reproducibility. While some of the other improvements described in the related Kromoscopy patents, such as the use of detectors utilizing congruent sampling (see U.S. Pat. No. 5,434,412 entitled IMPROVEMENTS IN NON-SPECTROPHOTOMETRIC MEASUREMENT OF ANALYTE CONCENTRATIONS AND OPTICAL PROPERTIES OF OBJECTS) or coded illumination (see U.S. Pat. No. 5,424,545 entitled NON-INVASIVE NON-SPECTROPHOTOMETRIC INFRARED MEASUREMENT OF BLOOD ANALYTE CONCENTRATIONS) improve accuracy and reproducibility, any variation in the viewed sample can lead to reproducibility problems.

The use of pulsatile measurements (see U.S. Pat. No. 5,434,412 entitled IMPROVEMENTS IN NON-SPECTROPHOTOMETRIC MEASUREMENT OF ANALYTE CONCENTRATIONS AND OPTICAL PROPERTIES OF OBJECTS) is based, in part, on the hypothesis that the change in blood volume caused by the arterial pulse provides the only variation against a constant optical background. While this is a fairly good approximation, in reality there are variations in venous pressure and volume produced by a variety of physiological variables which means that the background is not really constant. This is particularly prevalent at the measuring site of choice for most non-invasive measurements, the finger. The flow of blood through the finger involves a complex network of arteries, veins, capillaries, arteriovenous anastomoses, venules, and arterioles. In particular, blood flow is partially shunted through the anastomoses, primarily to control heat loss through the extremities, at a rate which varies depending on blood pressure and temperature. For example, as the finger is chilled, the flow through the shunt vessels decreases.

Non-invasive measurements making use of the pulsatile nature of blood in general cannot distinguish between pulsatile flow in the arterial circulation and time-variant changes in flow, e.g., pulsatile flow, in the venous circulation, as the transit time for the pressure pulse is extremely short compared to the pulse frequency. Therefore, any pulsatile flow in the venous circulation is seen as a part of the overall pulsatile flow. If the constituent or constituents of interest have different concentrations in arterial and venous blood, venous pulsation can cause an error in measurement, and variability in venous pulsation produces a consequent variability in the measurement.

When the finger is elevated above the level of the heart, the larger venous vessels and some of the anastomoses will drain by gravity toward the heart. This reduction in venous volume and in the volume of the shunt vessels thereby reduces the shunting effect and the venous pulse variation. The result of this manipulation is therefore both a stabilization of the optical background and a reduction in the amount of venous pulsation.

For measurements of oxygen saturation in arterial blood via pulse oximetry, the reduction in venous pulsation has been theorized as an explanation for some of the effects found (See Kim et al. "Pulse Oximetry and Circulatory Kinetics Associated with Pulse Volume Amplitude Measured by Photoelectric Plethysmography." Anesth. Analg. 65: 1333–9 (1986)). However, this concept has not been tested or even suggested with respect to concentration measurements. The variation found by Kim et al. was quantified using pulse oximetry measurements, which are measurements of ratios of oxygenated to deoxygenated hemoglobin rather than absolute concentration measurements, and were sufficiently small to be within the normal variance of the instrument. Accordingly, there is not even a suggestion in Kim et al. that elevation would provide any benefit in reproducibility.

Accordingly an object of the invention is to provide a method of providing increased reproducibility of results in non-invasive measurements of concentration.

Another object of the invention is to provide a method of improving accuracy of results of a non-invasive measurement.

These and other objects and features of the invention will be apparent from the following description and the drawing.

SUMMARY OF THE INVENTION

The present invention features a method of improving the reproducibility of non-invasive measurements for concentration of a variety of substances in blood. The method is based, in part, on the recognition that reducing the variability of the venous volume and the effects of venous pulsations can lead to an improvement in the overall variance of measurements when an arterial pulsatile measurement is utilized.

The method includes the steps of placing the portion of the body in which a concentration measurement is to be made in a position whereby it is elevated above the heart during the measurement cycle, taking an optical measurement of the body portion while elevated, and calculating concentration from the optical measurement. While any type of optical measurement of the cardiac pulse such as spectroscopic measurements can be utilized and will be improved by this method, Kromoscopic type measurements are preferred. The preferred optical ranges are near infrared measurements and the preferred body portion is a finger. The measurements should be made such that multiple measurements may be made on the same arterial pulse, thereby minimizing the variance.

The preferred optical system for use with the method of the invention utilizes broad band illumination and detection, with multiple detectors or multiple illumination sources having coded detection thereof. In another variant, polarized light is used as the illumination source and changes in the polarization or amount of polarized light having the same polarization are detected. Preferably, congruent illumination and/or congruent sampling are used and a restricted solid angle is used for measurement. Details of preferred Kromoscopic and spectroscopic apparatus, methods and methods of minimizing variance, other than the elevation aspect, are found in U.S. Pat. Nos. 5,321,265; 5,424,545; 5,434,412; 5,818,044; 5,818,048; 5,672,875; and U.S. patent application Ser. No. 09/073,574. Disclosures of all of the aforementioned patents and patent application are hereby incorporated by reference.

For purposes of the present invention, the following terms are used:

The term "optical" includes not just use of visible light but also infrared, ultraviolet, or any type of radiation source which is utilized for illumination and/or detection. Optical also includes polarized light, fluorescence, and other types of radiant energy detection and illumination known to those skilled in the art.

The term "elevating" means arranging such that the body part is measured is at a physical location above the heart, sufficient to cause drainage of venous blood from the body part. This may be accomplished by raising the hand above the heart with the patient vertically or horizontally positioned so long as the heart itself is sufficiently lower than the body portion being measured.

The terms not specifically defined herein are given their ordinary meaning except to the extent they are defined differently in one of the patents which is incorporated herein by reference, or if there is a different usage common in the industry.

DETAILED DESCRIPTION OF THE INVENTION

Figure 1:
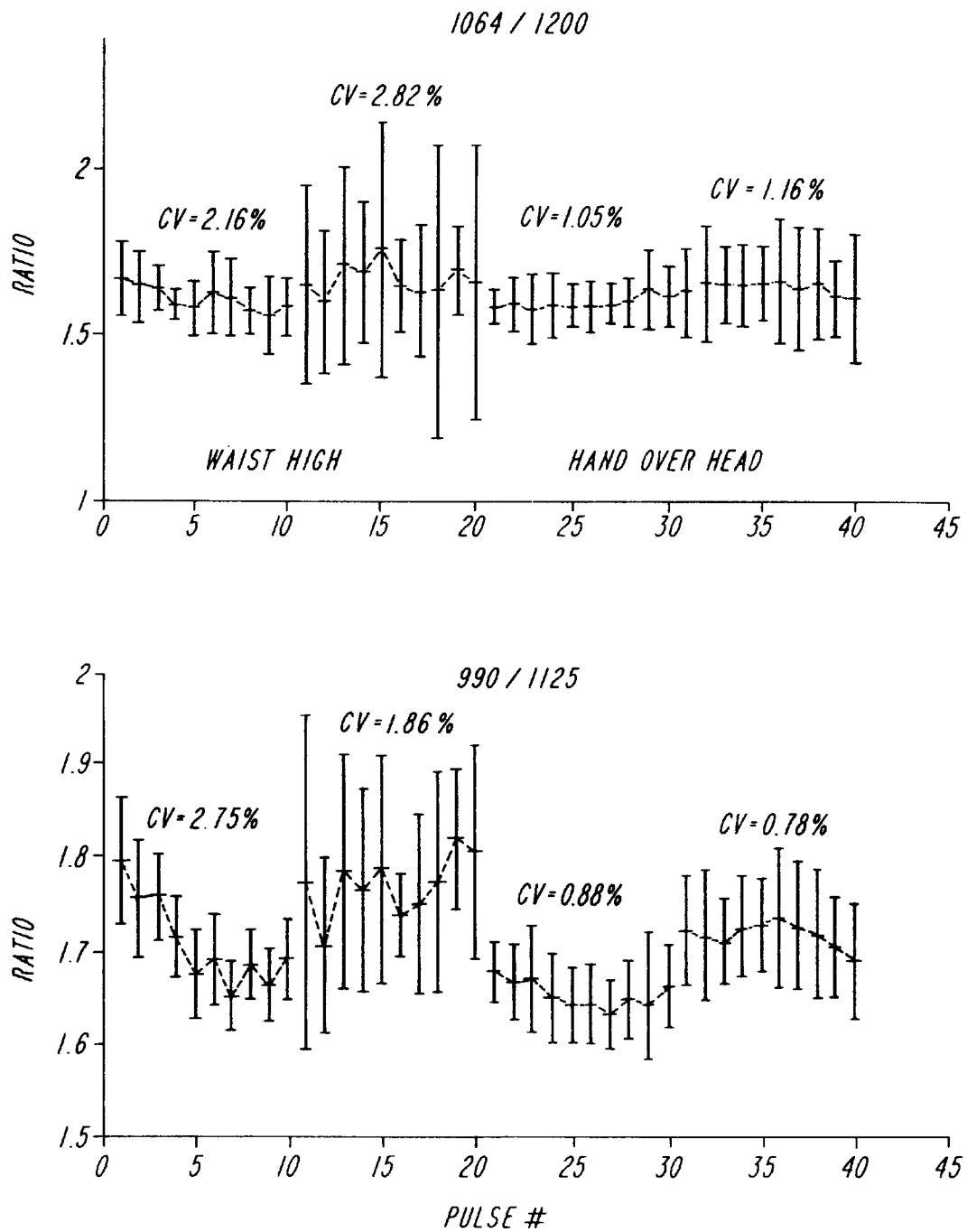
FIG. 1 shows a graph of ratios of voltage output at various wavelengths showing data taken at elevated and non-elevated positions.

The present invention concerns a method for improving the reproducibility of non-invasive concentration measurements. The method is based, in part, on the recognition that elevating the body portion being measured above the heart can lead to a reduction in the variability of the background, specifically the "steady-state" venous measurements upon which an arterial pulse measurement forms a variation. While it is believed that this improvement in reproducibility is based on a reduction in the venous pulse due to minimizing shunting through the anastomoses, it is not necessary for the practice of the invention for this scientific explanation to be accurate. Empirically, it has been found that elevating the body portion being measured above the heart leads to the requisite reproducibility improvement.

Numerous apparatus described in the non-invasive testing literature, including classic spectroscopic instruments could be used for the present invention. The preferred apparatus and methods are described in the Kromoscopy patents which had previously been incorporated by reference. Briefly, the finger, or the body portion in which the concentration is being measured, is placed in a sample chamber to hold it in position and the sample chamber is elevated to a position above the heart. The finger is illuminated with broad beam radiation and the radiation transmitted, reflected or transflected from the finger is detected. Preferably, transmission measurements are used so that the detector (or detectors) is placed on the opposite side of the finger from the illuminating radiation. Better measurements are obtained if congruent illumination and/or detection is utilized; that is, the path between each illumination source and the detector is arranged to be geometrically equal and passing through the same point of the finger so there is no variation in pathlength or difference in amount of absorbers from channel to channel. The preferred illuminating radiation is near infrared radiation, preferably in the 700–2200 nm range. While any amount of elevation above the heart should provide some of the beneficial effects, an elevation of at least 6 inches above the heart (and preferably about 18 inches above the heart) seems to provide a better result.

The following, non-limiting examples will further explain the invention and its advantages.

EXAMPLE 1

In this experiment, a Kromoscopic apparatus having a 20 watt QTH lamp with a blocking filter limiting the light output to the region from 700 to 1400 nm was used to illuminate a fingertip with the nail facing the source. After transmittal of the light through the finger, it was detected by four detectors, each being an indium gallium arsenide (InGaAs) detector with a different filter in front of each detector. The filters had peak transmission at 990 nm, 1064 nm, 1125 nm, and 1200 nm respectively. The detectors are arranged such that congruent detection is achieved; that is, they all see the same optical path. In this series of runs, the finger was either set approximately 6 inches below the heart or approximately 18 inches above the heart.

FIG. 1 shows the results of these experiments, in the form of the ratios of the pulsatile modulations at pairs of wavelengths, a presentation that minimizes variability due to changes in optical pathlength and other extraneous variables, and has been found to correlate with concentration changes. FIG. 1's upper graph shows the results for the 1064/1200 nm ratios while FIG. 1's lower graph shows the results for the 990/1025 nm ratios. The CV is the run-to-run variance while the height of the individual bars indicates the variance within each run.

As can be seen from this figure, both the run-to-run variance and the intra-run (i.e., pulse to pulse) variance are reduced by elevating the hand 18 inches above the heart. In particular, this test had the hand at waist height and showed CVs of 2.16% and 2.82% for the 1064/1200 ratio while with the hand over the head, the CVs were 1.05% and 1.16% for the same ratios. In addition, the inter-run variance, as seen by the size of the bars, is much less. With respect to the 990/1125 ratios, the CVs at waist height are 2.75% and 1.86%, while when the finger is held over the head, the CVs were reduced to 0.88% and 0.78%.

This example shows that using the Kromoscopic configuration disclosed in the previous patents combined with finger elevation, one can improve the reproducibility of the results.

EXAMPLE 2

In this example, a different experimental setup was used. A Nellcor pulse oximeter was used to supply the illumination and detection system but the analog signals from Nellcor detectors were routed to a separate data acquisition system, one similar to that used in Example 1. The index finger of the left hand was used in the pulse oximeter sample chamber. This configuration permits the measurement of pulse oximetry data using a data acquisition system with higher fidelity than that of the commercial device.

Figure 2:
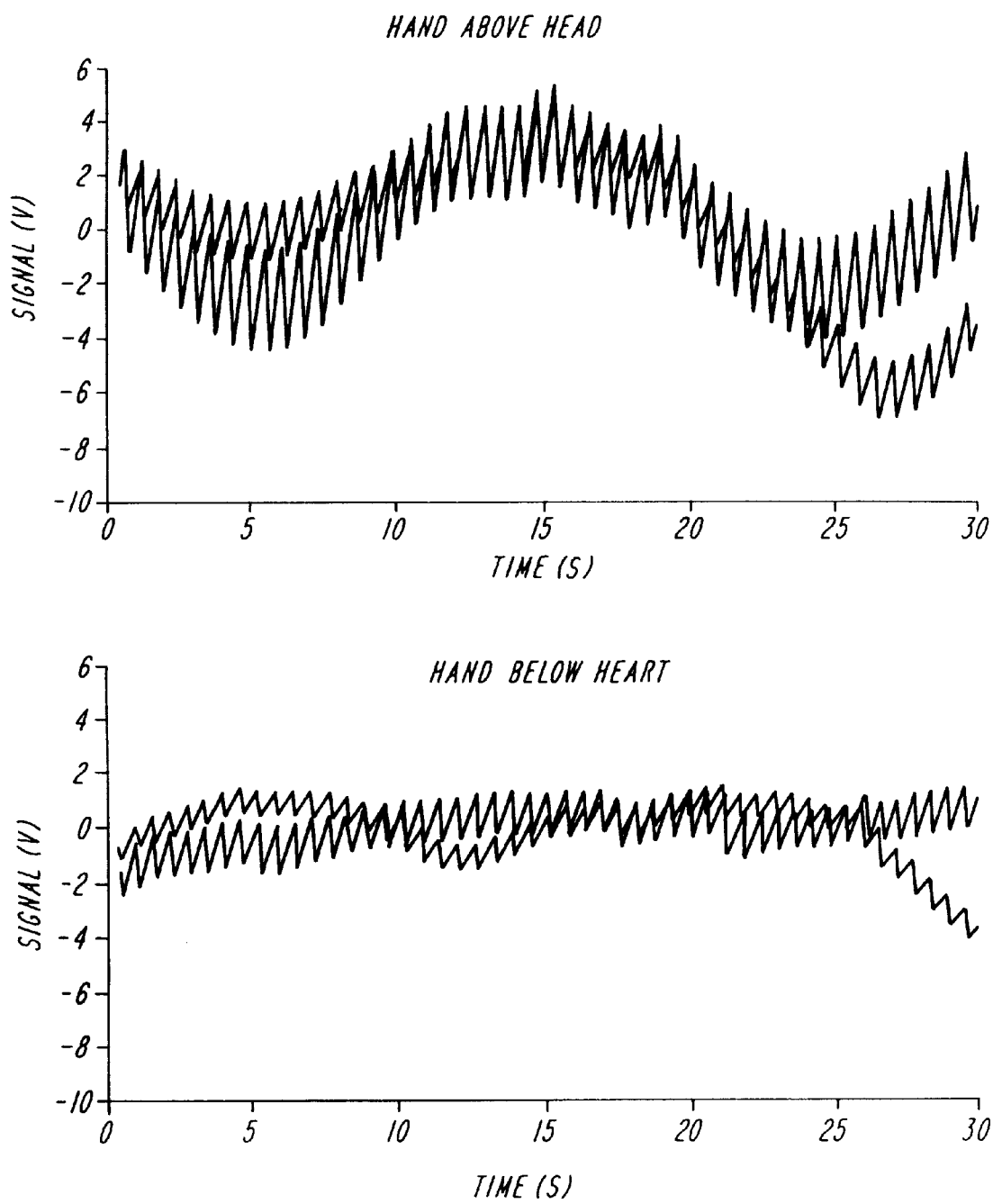
FIG. 2 shows a tracing of voltage output in elevated and non-elevated positions using a Nellcor pulse oximeter.

The finger was illuminated and the transmitted light collected by the Nellcor apparatus. This generated an output voltage from the photoelectric cell in the Nellcor device. Voltage was measured for 30 seconds using this setup. FIG. 2 illustrates the output signal, in volts, for signal collected from with this experimental setup with the hand above the head (upper graph) and the hand below the heart at approximately waist height (lower graph). As can be seen from this data, the signal amplitude is larger, and is more consistent, with the hand above the heart than below the heart.

Figure 3:
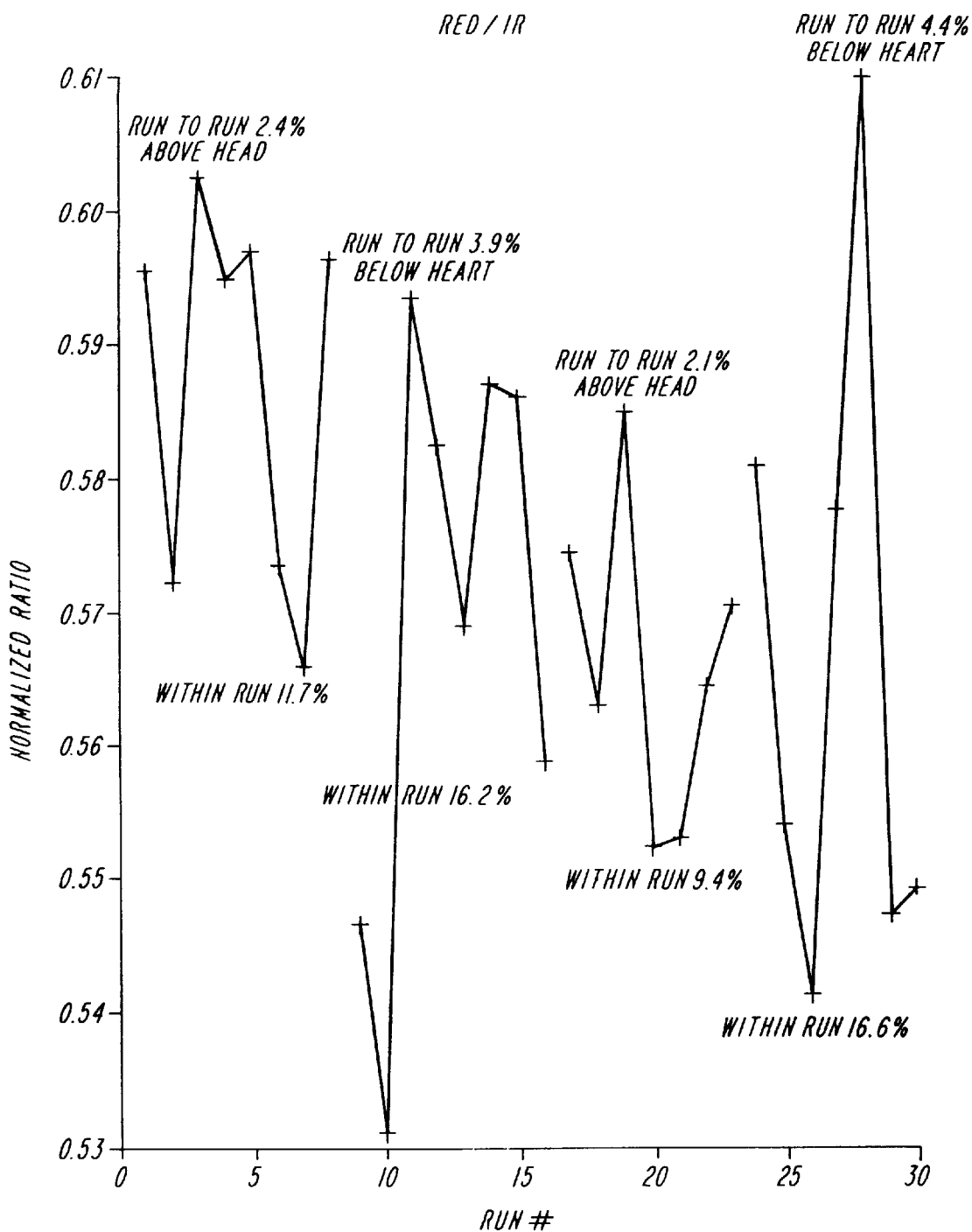
FIG. 3 shows the data of FIG. 2 normalized by wavelength.

FIG. 3 is a normalization of the data of FIG. 2. As is shown by FIG. 3, the run-to-run variation for the data when the finger is held above the heart (in particular above the head) was 2.4% and 2.1%. Similarly, the within run variability was 11.7% and 9.4% with the hand held above the head. In contrast, with the hand held below the heart, the run-to-run variability was 3.9% and 4.4%, respectively, and the within run variability was 16.2% and 16.6%. This example shows that the variability of other optical methods performing measurements on the cardiac pulse is also reduced when elevation of the hand above the heart is used.

The foregoing examples are not intended to limit the invention but rather to merely illustrate it.

The fact that both the run-to-run and within run variability are reduced is surprising. The signal increases with elevation of the hand but this means that the amount of absorption by the sample is decreased. Accordingly, the absolute difference between the background and the signal decreases. It appears that the advantage in reducing the background levels, in particular the variability in those background levels, more than compensates for this reduction in absolute signal.

Those skilled in the art will find other modifications and to the present invention. Those other modifications are encompassed within the scope of the following claims.

What is claimed is:

1. A method for minimizing variations in non-invasive measurements of concentration of a constituent of interest within a body part of a patient, said method comprising the steps of:

elevating said body part such that it remains at least 6 inches above the heart of the patient during the measurement cycle;

illuminating said body part with optical radiation;

measuring radiation transmitted, reflected or transflected from said body part;

calculating the concentration of said constituent of interest within said body part of said patient from the measured value of radiation.

2. The method of claim 1 further comprising the step of maintaining said body part elevated relative to the heart for a predetermined period of time prior to non-invasively measuring said concentration of said constituent of interest.

3. The method of claim 1 wherein optical radiation in said illuminating step comprises near infrared radiation and said measuring step utilizes a plurality of detectors, at least one of said detectors being selected to be sensitive to a portion of said infrared illuminating radiation.

4. The method of claim 3 wherein said illumination step comprises utilizing broad band illumination.

5. The method of claim 3 wherein said detection step comprises utilizing detectors arranged for congruent sampling.

6. The method of claim 1 wherein said at least a portion of said measurement step comprises taking measurements during an arterial pulse cycle and wherein multiple measurements are made during the same arterial pulse.

7. The method of claim 1 wherein said illumination step comprises utilizing multiple illumination sources and each source utilizes a coded signal upon its illuminating radiation.

8. The method of claim 1 wherein said illumination step comprises utilizing polarized illumination.

9. The method of claim 1 wherein said detection step comprises utilizing detectors having at least partial overlap in wavelength.

10. The method of claim 1 wherein said constituent of interest comprises glucose.

11. The method of claim 1 wherein said constituent of interest comprises hemoglobin.

12. The method of claim 1 wherein said body part comprises a finger.

13. The method of claim 1 wherein said body part is elevated at least 18 inches above the heart during the measurement cycle.

* * * * *